(12) United States Patent
Augier et al.

(10) Patent No.: US 9,333,442 B2
(45) Date of Patent: May 10, 2016

(54) LIQUID-LIQUID EXTRACTION COLUMN CONTAINING TWO DISTINCT TYPES OF PLATES

(71) Applicant: IFP Energies nouvelles, Rueil-Malmaison (FR)

(72) Inventors: Frederic Augier, Saint Symphorien d Ozon (FR); Damien Leinekugel le Cocq, Lyons (FR); Romina Digne, Lyons (FR); Arnaud Baudot, Vernaison (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 0 days.

(21) Appl. No.: 14/080,832

(22) Filed: Nov. 15, 2013

(65) Prior Publication Data

US 2014/0142342 A1 May 22, 2014

(30) Foreign Application Priority Data

Nov. 20, 2012 (FR) .................................... 12 03120

(51) Int. Cl.
| | |
|---|---|
| *B01D 11/04* | (2006.01) |
| *C10G 21/00* | (2006.01) |
| *C10G 19/04* | (2006.01) |
| *C07C 319/30* | (2006.01) |
| *B01D 3/22* | (2006.01) |
| *B01D 3/20* | (2006.01) |
| *B01D 11/00* | (2006.01) |

(52) U.S. Cl.
CPC ................ *B01D 11/043* (2013.01); *B01D 3/20* (2013.01); *B01D 3/22* (2013.01); *B01D 11/00* (2013.01); *C07C 319/30* (2013.01); *C10G 21/00* (2013.01)

(58) Field of Classification Search
CPC ............. B01D 11/043; B01D 11/0426; B01D 2011/002; B01D 3/22; B01D 3/20; B01D 11/00; C10G 21/00; C07C 319/30
USPC ......... 210/511, DIG. 5, 634; 196/14.52, 14.5; 261/113
See application file for complete search history.

(56) References Cited

U.S. PATENT DOCUMENTS

| | | | |
|---|---|---|---|
| 2,794,711 A | 6/1957 | Hall et al. | |
| 2,895,809 A * | 7/1959 | Pohlenz | .................... 422/255 |
| 3,143,482 A * | 8/1964 | McLeod | ................. B01D 3/22 |
| | | | 202/158 |
| 4,039,389 A | 8/1977 | Christman | |
| 4,081,354 A * | 3/1978 | Christman | .................... 208/235 |
| 4,234,544 A * | 11/1980 | Christman | .................... 422/256 |
| 5,393,429 A * | 2/1995 | Nakayama et al. | ........... 210/634 |
| 6,029,956 A * | 2/2000 | McGrath | ................. B01D 53/18 |
| | | | 261/114.1 |

FOREIGN PATENT DOCUMENTS

EP 0541005 A2 5/1993

OTHER PUBLICATIONS

Search Report from Priority Patent Application No. FR 12/03120 dated Jul. 17, 2013.

* cited by examiner

*Primary Examiner* — Krishnan S Menon
*Assistant Examiner* — Waqaas Ali
(74) *Attorney, Agent, or Firm* — Millen, White, Zelano, Branigan, P.C.

(57) ABSTRACT

The present invention describes a liquid-liquid extraction column with perforated plates and downpipes, having a majority of so-called "open" plates and a minority of so-called "closed" plates, the two types of plates differing in the degree of perforation. Application of the said column to the treatment of liquid-liquid systems with time-variable coalescence.

13 Claims, 5 Drawing Sheets

LIQUID-LIQUID EXTRACTION COLUMN CONTAINING TWO DISTINCT TYPES OF PLATES

FIELD OF THE INVENTION

The invention relates to the field of liquid-liquid extraction or solvent extraction operations, involving contacting a hydrocarbon-containing phase with a phase that is partially immiscible with the hydrocarbon feedstock and contains an aqueous fraction.

The invention is particularly suitable for the extraction of sulphur compounds from a hydrocarbon phase by using an aqueous sodium carbonate solution (10-20 wt %), the hydrocarbon phase being the dispersed phase.

EXAMINATION OF THE PRIOR ART

The principle of solvent extraction between two partially immiscible liquid phases has been known for several decades. If a raffinate phase containing the solute is contacted with an extract phase containing no (or only a small amount of) solute, a transfer of solute from one phase to the other takes place until a thermodynamic equilibrium between the two phases is reached.

The phenomenon is greatly assisted if, at the thermodynamic equilibrium, the concentration of solute in the extract phase is greater than in the raffinate phase. The concentration ratio between these two phases at equilibrium is called the partition coefficient.

A conventional implementation of the liquid-liquid extraction consists in contacting the two liquids in counter-current, that is to say in opposite flow directions. In the case of extraction in a vertically arranged column one then speaks of a light phase and a heavy phase.

A very common case is that of systems consisting of an organic or hydrocarbon-containing phase and an aqueous phase. In this case the aqueous phase is very often the heavy phase.

In liquid-liquid extraction a distinction also has to be made between the continuous phase and the dispersed phase.

The continuous phase has a flow behaviour that is as close as possible to piston flow, i.e. without back mixing.

The dispersed phase has a flow that overall is counter-current to that of the continuous phase and passes through a system of perforated plates (trays) that allows the formation of droplets, these droplets coalescing so as to form a coalesced layer underneath each perforated plate when the dispersed phase is the light phase (above each plate when the dispersed phase is the heavy phase). The exchanges of matter between the continuous phase and dispersed phase essentially take place between the droplets of the dispersed phase and the continuous phase flowing over each plate.

The counter-current implementation enables a plurality of successive theoretical stages to be arranged in the column and thereby achieve an extraction efficiency that is greatly superior to that obtained with a single stage corresponding to the thermodynamic equilibrium.

A more detailed description of liquid-liquid extraction operations is provided in numerous specialised works, including *Handbook of Solvent Extraction* by Lo, Baird & Hanson, Krieger Publishing Company, Malabar, 1991, or *Transport Phenomena in Liquid Extraction* de Laddha & Degaleesan, Tata McGraw-Hill Publishing Co Ltd, 1976.

The concepts of theoretical stages are in particular described there, which is an important factor for understanding the importance of the invention.

Numerous extraction technologies are based on the dispersion of one phase in the other phase, and one then speaks of dispersed phase and continuous phase. The dispersed phase may be the heavy phase or light phase.

When the partition coefficient of a solute to be extracted is very high, i.e. the solute is very easily transferred to the extract phase, the counter-current liquid-liquid extraction columns are operated with a very low extract phase flow rate compared to the raffinate phase flow rate. As a result one of the two liquid phases moves in the column at an average velocity that is very low compared to the other phase. In this case particular attention must be paid to the hydrodynamics in the column, since there is a serious risk that the column will not operate efficiently and a theoretical stage will no longer be achieved. The benefit of counter-current operation may be reduced on account of an extraction efficiency lower than expected.

For example, when the dispersed phase is the phase having the greater flow rate the displacement of the droplets may possibly entrain a small amount of continuous phase in their wake, which tends to displace the said continuous phase in the opposite direction to its average movement.

In the extreme case the flow of the continuous phase becomes comparable to that of a perfectly stirred single reactor, and the solute concentrations in the continuous phase are homogeneous in the column. The number of theoretical stages of the apparatus is then 1. When the ratio of volumetric flow rates between the extract phase (E) and raffinate phase (R), denoted E/R, exceeds 5 or is less than 0.2, an extraction column technology involving plates and downpipes is often used.

This technology is based on the division of the column into compartments separated from one another by a perforated plate provided with a downpipe. The purpose of the plate is to force the dispersed phase to coalesce on one side of the plate and to re-disperse this same phase on the other side, through the perforations of the plate.

This enables a unidirectional flow of the dispersed phase between one compartment and the following compartment to be ensured. Likewise, the fact that a coalesced layer of initially dispersed phase is formed on one side of the plate prevents the passage of the continuous phase through the perforations of the plate.

The number and the size of the perforations of the plate are chosen so as to produce a loss of feedstock that will cause the formation of a coalesced layer of dispersed phase having a desired thickness under given operating conditions.

For example, in the case of a light dispersed phase the perforations may be chosen so as to form a layer of coalesced light phase under each plate, the layer typically having a thickness of between 40 mm and 100 mm.

The coalesced layer should be sufficiently thick over the whole cross-section of the column so as to prevent the passage of the continuous phase through the perforations of the plate. However, too thick a layer has an adverse effect on the extraction efficiency, since this reduces the volume in which the transfer between the liquid phases takes place, i.e. the volume in which the droplets of dispersed phase are present.

The plate of a liquid-liquid extraction column is generally provided with a downpipe whose geometry and arrangement are chosen so as to allow the movement of the continuous phase from one compartment to the other, in the opposite direction to the movement of the dispersed phase.

In addition, the geometry of the downpipe is chosen so as to restrict the entrainment of droplets of dispersed phase, such an entrainment adversely affecting the overall performance of the extraction by reducing the number of associated theoretical stages. A criterion of maximum velocity in the downpipe is therefore often imposed so as not to entrain droplets of dispersed phase.

The successive plates of the extraction column are positioned in a staggered arrangement so that the continuous phase travels the whole width of the compartment before returning to a new downpipe.

D-shaped, more generally arcuate-shaped, downpipes are often used on account of their simplicity and the fact that they enable a large proportion of the diameter of the column to be covered, thereby minimising dead volumes. The chord of the downpipe is normally fixed between 0.3 and 0.8 times the diameter of the column.

Several problems may be encountered in the dimensioning and operation of extraction columns with perforated plates and downpipes.

If the flow rate of dispersed phase is greater than ten times the flow rate of continuous phase, it becomes difficult to design downpipes enabling the entrainment of droplets to be prevented, having a chord representing a large fraction of the diameter of the column, and at the same time enabling the flow of the continuous phase to be sufficiently compartmentalised so as to prevent the remixing of the continuous phase in the column. It is then sometimes suggested to employ plates having downpipes with very small cross-sections, as mentioned in the patents U.S. Pat. No. 4,207,174 and U.S. Pat. No. 6,749,741B1.

In order to limit the entrainment of droplets, the compartments are equipped with chicanes and internal partitions that restrict the zone of the compartment in which contact between the liquid phases is possible. As a result, this type of plate offers a small contact surface between the phases, which has an adverse effect on the efficiency of the extraction.

The surface tension of the treated liquid-liquid system is an important parameter since it determines the size of the droplets that are formed and thus their terminal velocity. This parameter therefore determines the maximum permitted velocity in the downpipes without causing entrainment of dispersed phase, and thus determines the minimum cross-section of the downpipes.

Another problem that is encountered is associated with the ease of coalescence of the droplets of dispersed phase. If the system is highly coalescent, a small thickness of dispersed phase is necessary in order to re-coalesce the droplets and form a continuous layer before passing through the plate.

On the other hand if the coalescence between the droplets is slow, it is necessary to ensure a certain contact time between droplets before they coalesce. As a result the plates are then only efficient if the layer of dispersed phase is large underneath or on the plates, depending on whether the dispersed phase is respectively light or heavy.

The overall cross-section of the perforations must then be reduced in order to increase the loss of feedstock associated with the passage through the plates and thereby increase the thickness of coalesced phase. This consequently often necessitates increasing the inter-plate distance.

It can easily be understood that, depending on the coalescent or slightly coalescent nature of the system, and depending on its surface tension, the optimal plate will not have the same geometry.

A plate designed so as to treat in the majority of cases a system that is highly coalescent and has a high surface tension may perform very poorly if there is a drop in surface tension on account of the entrainment of droplets in the downpipe, or in case of a slower coalescence on account of the passage of continuous phase through the plates.

The present invention describes a liquid-liquid extraction column equipped with plates and downpipes that enables the extraction performances to be maintained despite possible changes in surface tension and a more or less coalescent nature of the system.

The document U.S. Pat. No. 4,081,354 discloses a liquid-liquid extraction process having variable flow rates of dispersed phase. It does not specify any variation in the degree of opening of the plates that are used.

The document U.S. Pat. No. 2,794,711 discloses a device enabling two liquids to be intimately contacted with one another by means of contact plates and dispersion baffles. No details of a possible difference in the degree of opening of the plates is given in this document.

BRIEF DESCRIPTION OF THE INVENTION

The invention relates to a counter-current liquid-liquid extraction column having perforated plates with downpipes requiring a limited number of theoretical stages ($2 \leq NET \leq 4$), and in which the partition coefficient of the solute to be extracted is very high, so that the flow rate of extract phase is very low compared to the flow rate of raffinate phase.

The partition co-efficient is defined as the ratio of the molar concentration of solute in the extract to the molar concentration of solute in the raffinate at equilibrium. In the context of the present invention this partition coefficient is $\geq 50$.

The object of the invention is to ensure a good operation of the extraction column, even in the case of variations in properties of the treated liquid-liquid system (surface tension, coalescent nature of the dispersed phase, etc).

The apparatus according to the invention combines in a novel manner two types of perforated plates with downpipes having highly distinct geometries and functions.

The two types of plates differ both in the perforation cross-section and in the downpipe cross-section. In the following description we therefore define the so-called "open" plate as having a specified perforation cross-section and a specified downpipe cross-section, and the so-called "closed" plate as having a perforation cross-section and a downpipe cross-section smaller than those of the open plate.

The invention is based on the use of a majority of open plates in the column, and a limited number, or minority, of closed plates distributed within the open plates. A closed plate is always contained between two open plates. The number of open plates is between 4 and 25, preferably between 6 and 20, and the number of closed plates is between 1 and 3 and preferably between 1 and 2.

The open plates are designed so as to obtain an optimal operation in the presence of a coalescent system and at high surface tension, i.e. having a coalescence time between two drops in contact of less than 2 seconds, and a surface tension greater than 15 mN/m.

On account of this, the thickness of coalesced layer is maintained between 50 mm and 100 mm.

The downpipe of an open plate is chosen so that the velocity of the dispersed phase does not exceed a value between 5 mm/s and 60 mm/s. The maximum value that must not be exceeded, situated in the range from 5 to 60 mm/s, depends on the physico-chemical properties of the liquid-liquid system, and in particular its surface tension.

The closed plate has a perforations cross-section that is smaller than that of an open plate, the coefficient of reduction of the perforation being between 0.2 and 0.8 and preferably between 0.3 and 0.5 times the perforation of an open plate.

The perforation of an open plate is typically between 2% and 6% related to the empty cross-section of the column, and preferably between 3% and 5% of the empty cross-section of the column.

As a result the layer of coalesced dispersed phase underneath a closed plate has a thickness between 100 mm and 1000 mm, preferably between 300 mm and 800 mm.

The cross-section of the downpipe of a closed plate is chosen so as to be between 0.25 and 1 times the cross-section of the downpipe of the open plates.

The invention is particularly well suited to the case of a liquid-liquid system in which the coalescent nature develops over time. This type of variations in properties may be associated with various phenomena: a change of feedstock, the use of a discontinuous pre-treatment, etc. More specifically, the invention is particularly suitable for systems having a rapid coalescence for most of the time, but which from time to time become slightly coalescent or even foaming.

In this case, an apparatus according to the prior art equipped only with open type plates may exhibit greatly reduced separation performances on account of the poor coalescence of the dispersed phase, and on account of the entrainment of the continuous phase by the perforations of the plate. As explained in the paragraph describing the prior art, these two phenomena reduce the number of theoretical stages of the apparatus.

When the system is slightly coalescent, the simplest solution that the person skilled in the art would consider is to employ an apparatus equipped only with plates that are more closed, creating a longer contact time of the phase to be coalesced before passing to the perforated plate. However, such an apparatus would then not be very efficient if the liquid-liquid system momentarily underwent rapid coalescence.

Starting from a rapid coalescence system, the invention enables good performances to be maintained even if the system intermittently becomes less coalescent. In the same way, starting from a slow coalescence system the invention enables good performances to be maintained even if the system intermittently undergoes rapid coalescence.

DETAILED DESCRIPTION OF THE INVENTION

More specifically the invention may be defined as a counter-current liquid-liquid extraction column having perforated plates with downpipes requiring a limited number of theoretical stages ($2 \leq NET \leq 4$), and within which the partition coefficient of the solute to be extracted is greater than or equal to 50.

The said extraction column is dimensioned for feedstock readily coalescent for most of the time, but also allows the treatment of slightly coalescent or readily coalescent feedstocks, but which may intermittently become less well coalescent or even slightly coalescent. The extraction column thus has a very broad range of application as regards the coalescent nature of the liquid-liquid system that is used, and it is this that clearly distinguishes the column from extraction columns of the prior art.

The said column comprises two distinct types of plates, namely a majority of open plates defined by a degree of perforation p % between 2% and 6%, and a minority of closed plates defined by a degree of perforation between 0.2 and 0.8 times, and preferably between 0.3 and 0.5 times that of the open plates. The perforation percentages are in relation to the empty cross-section of the column. Preferably the degree of perforation of the open plates is between 3% and 5%.

Each closed plate is situated between two open plates, and the minority of closed plates are situated in the middle part of the column, i.e. by dividing the column into two substantially equal portions, numbered 1 and 2 from the top downwards, in the lower part of the portion 1 or the upper part of the portion 2.

According to a preferred variant of the present invention, the downpipes associated with the closed plates have cross-sections between 0.2 and 1 times that of the downpipes of the open plates.

According to another preferred variant the downpipes of the closed plates have a variable cross-section in the sense that they have a first cross-section, followed in the flow direction of the liquid by a second cross-section of larger size than the first cross-section. According to an also preferred variant of the present invention, a closed plate occupies the space corresponding to two open plates, and in this case the downpipe associated with the said closed plate comprises a part crossing the column substantially along a diameter, so that the outlet of the said downpipe is located opposite its inlet.

According to another variant of the present invention, a packing layer designed to promote coalescence is arranged under some closed plates, the thickness of the said layer being less than the height of the downpipe of the closed plate in question.

Preferably the number of open plates is between 4 and 25, and most preferably is between 6 and 20. The number of closed plates is preferably between 1 and 3, and most preferably between 1 and 2.

In general the extraction column according to the present invention enables liquid-liquid systems to be treated in which the dispersed phase may be either the light phase or the heavy phase.

The extraction column according to the present invention can be applied particularly well to the extraction of sulphur-containing compounds from a hydrocarbon phase by a 10-20 wt. % aqueous solution of sodium carbonate, the hydrocarbon phase being the dispersed phase.

Preferably the liquid-liquid extraction column according to the present invention can be applied to systems in which the ratio of the flow rate of the extract phase (E) to the raffinate phase (R) is between 5 and 50 or (exclusively) between 0.02 and 0.2.

Figure 1:
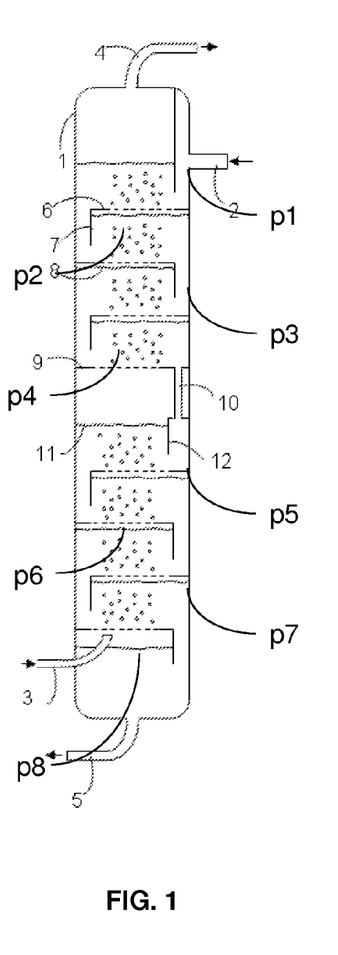
FIG. 1 shows an overall view of an extraction column according to the invention in the case of a dispersed light phase.

The following detailed description is given with reference to the accompanying figures. FIG. 1 shows a liquid-liquid extraction column according to the invention, supplied with a heavy phase via the pipe 2 and with a light phase via the pipe 3.

The heavy phase, which is the continuous phase, leaves the bottom of the column via the pipe 5, and the light phase, which is the dispersed phase, leaves the head of the column via the pipe 4.

The column is equipped with 7 open-type plates and one closed-type plate situated in the middle of the column. Numbering the plates 1 to N from the top downwards, the closed plate is No. 4 and the open plates are the plates 1 to 3 and 5 to 8.

Each open plate consists of a perforated plate (6) and a downpipe (7).

The loss of feedstock due to passage through the plates leads to the presence of a layer of coalesced dispersed phase (8) under each plate.

The closed-type plate consists of a perforated plate (9) and a downpipe (10).

The perforations of the closed plate are defined by a degree of perforation with respect to the perforations of an open plate. The degree of perforation of a closed plate is between 0.2 and 0.8 times that of an open plate, and is preferably between 0.3 and 0.5 times the said perforation of an open plate.

The cross-section and the shape of the downpipe of the closed plate may be constant over its whole length, or may vary as shown in FIG. 1.

Whether constant or variable, the cross-section of the downpipe of a closed plate is between 0.25 and 1 times the cross-section of the downpipe of an open plate.

The coalesced layer (11) formed underneath the closed plate is then larger than the coalesced layer (8) underneath the open plates, which may require a gap between a closed plate and the open plate situated therebelow, that is greater than the gap between two successive open plates.

Figure 2:
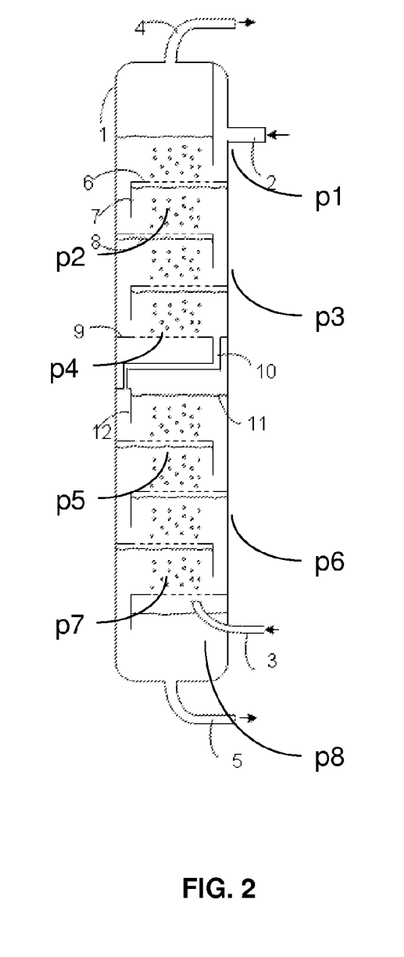
FIG. 2 shows an overall view of a column according to the invention in the case of modification of an existing column initially comprising perforated plates and conventional downpipes.

FIG. 2 illustrates the invention in the case of an existing extraction column initially equipped only with open-type plates. This case corresponds to the remodeling of an existing column in order to handle liquid-liquid systems that may be weakly coalescent from time to time.

In this case the implementation of the invention consists in modifying an open plate by plugging a fraction of the perforations so as to achieve a range from 0.2 to 0.8 times the initial perforation, and removing the lower open plate so as to leave a free space sufficient for the coalesced layer (11) of dispersed phase that is going to become larger following the reduction in the degree of perforation.

It is then also necessary to modify the downpipe (10) of the thereby formed closed plate so as to reduce its cross-section in a ratio that is between 0.25 and 1 times the cross-section of the downpipes of the open plates.

In order to maintain the orientation of the existing open plates, the downpipe (10) makes use of elbow pieces so as to conduct the liquid phase from the side opposite that of the said downpipe (10), as is shown in FIG. 2. One then speaks of a traversing downpipe, since the downpipe (10) comprises a slightly inclined part extending substantially over the width of the column. The downpipe (10) of the closed plate No. 4 communicates with the downpipe of the open plate situated below (plate No. 5), as is shown in FIG. 2.

The downpipe (12) of the open plate situated below the closed plate No. 4 can thus be preserved.

Figure 3:
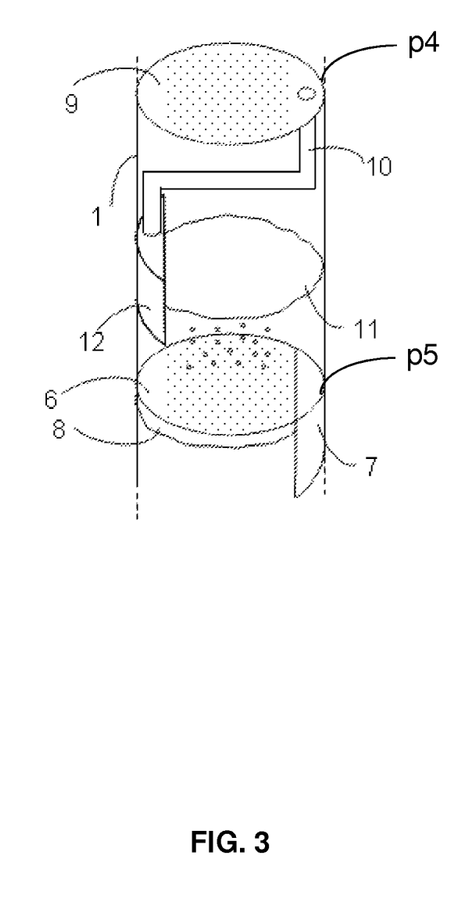
FIG. 3 shows a detailed view of a closed plate with a traversing downpipe according to the invention in the case of modification of an existing column.

FIG. 3 shows in more detail the perforated plate (9) of the upper closed plate, the downpipe of this plate having a first part (10) and a second substantially horizontal part, and the connection of the downpipe to the open plate situated below (lower plate) by means of a third vertical part (12) having a cross-section greater than that of the first part (10).

From FIG. 3 it can be also be seen that the thickness of the coalesced layer (11) underneath the upper closed plate is greater than the thickness of the coalesced layer (8) underneath the open plate situated below (lower plate).

Figure 4:
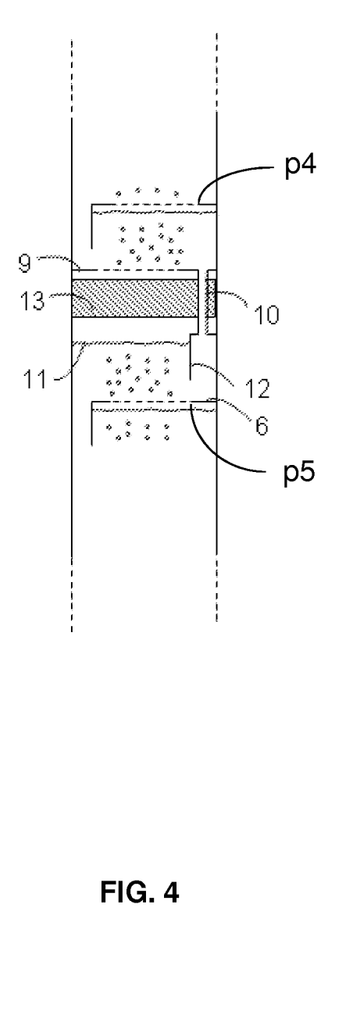
FIG. 4 shows a detailed view of the column according to the invention with the addition of a filtering agent underneath the closed plate.

FIG. 4 illustrates a particular embodiment of the invention. In order to facilitate coalescence between the droplets, a porous filtering agent (13) is introduced underneath the closed plate (9), which enables the performances of the invention to be improved in the case of a very slightly coalescent system.

The downpipe (10) than traverses the porous medium (13), following which it widens out into an end part (12) so as to supply the lower open plate (6).

The coalesced layer is normally situated below the plate (9), and the interface (11) between this coalesced layer and the liquid phase with dispersed droplets may be disposed below the packing (13).

Figure 5:
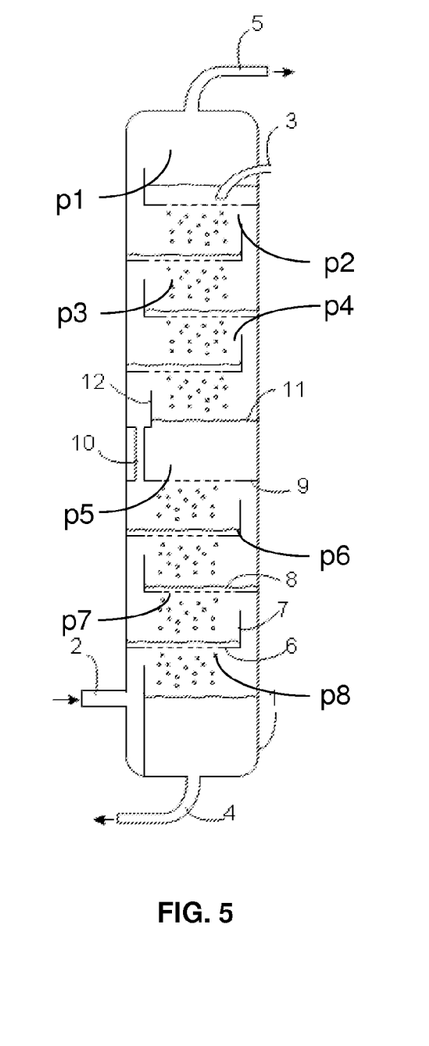
FIG. 5 shows an overall view of the column according to the invention in the case of a dispersed heavy phase.

FIG. 5 illustrates the invention in the case where the heavy phase is the dispersed phase. The light phase is introduced via the lower tube (2) and leaves via the upper tube (5).

The heavy phase is introduced via the upper tube (3) and leaves via the lower tube (4). The coalesced layer (8) is situated above each open plate such as (6).

The coalesced layer (11) is also situated above the closed plate (9), but is larger than the coalesced layer corresponding to an open plate.

The operation of the extraction column according to the invention is the same as in the case where the dispersed phase is the light phase.

The two technical differences compared to the case of the dispersed light phase are:
  The downpipes (10, 12) are then oriented upwardly.
  The possible coalescent medium (13) is situated above the closed plate.

COMPARATIVE EXAMPLE

The following comparative example is obtained by simulation.

The feedstock to be treated is a hydrocarbon containing 100 ppm of methanethiol.

The solvent used to extract the methanethiol is a 20% sodium carbonate solution.

The dispersed phase is the hydrocarbon phase.

The hydrocarbon and sodium carbonate flow rates are 150 and 10 m3/h respectively.

The extraction is carried out at 30° C. and under 10 bars absolute.

Three different apparatuses are used to perform the extraction.

The so-called "open plates" apparatus 1 is according to the prior art. This apparatus consists of an extraction column equipped with 15 perforated plates with downpipes, spaced 1 m apart and 3 m in diameter.

The perforations are 5 mm in diameter and the perforated surface area is equal to 3% of the cross-section of the column.

The downpipes have a surface area equal to 20% of the cross-section of the column. The apparatus 2, also according to the prior art, is a so-called "closed plates" apparatus. It is similar in every respect to the apparatus 1, but the perforated surface area is equal to 1% of the column cross-section, and the downpipe surface area is equal to 10% of the column cross-section.

The apparatus 3 is according to the invention. The apparatus consists of an extraction column equipped with 14 open-type plates, such as those used in the apparatus 1, and one closed-type plate, such as that used in the apparatus 2.

The closed plate is positioned at mid-height in the column, i.e. above the first 7 open plates and below the 7 remaining open plates.

When the liquid-liquid system has a rapid coalescence, fixed at 2 sec, the efficiency of an open-type plate is 20% compared to a theoretical stage, while that of a closed plate is 10%. When the liquid-liquid system has a slow coalescence, regarded in this case as 20 seconds, the efficiency of a closed plate is still 10%, whereas that of an open plate is greatly changed. In fact, the open plates then no longer ensure a counter-current flow since the heavy phase undergoes a very pronounced back-mixing through the plates. The result is that a series of successive open plates consisting of at least 5 plates then behaves like a single theoretical stage.

The presence of a carefully positioned closed-type plate enables the flow of the heavy phase to be compartmentalised.

The equivalent number of theoretical stages resulting from the three apparatuses, depending on the system in question, is given in Table 1 below:

TABLE 1

Number of equivalent theoretical stages for the apparatuses 1 to 3

|  | Apparatus 1 | Apparatus 2 | Apparatus 3 |
| --- | --- | --- | --- |
| Coalescent system | 2.8 | 1.4 | 2.68 |
| Slightly coalescent system | 1 | 1.4 | 2 |

The value of the invention can clearly be seen from Table 1. The performances of the column according to the invention (apparatus 3) are almost identical to those of the column with open plates (apparatus 1) in the case of a coalescent system, and are much superior to the two other columns (apparatuses 1 and 2) in the case of a slightly coalescent system.

The entire disclosures of all applications, patents and publications, cited herein and of corresponding French Application No. 12/03120, filed Nov. 20, 2012 are incorporated by reference herein.

The invention claimed is:

1. A counter-current liquid-liquid extraction column comprising:
    a column having a diameter and upper, middle and lower parts,
    a plurality of spaced perforated plates with associated downpipes, each downpipe having an inlet and an outlet,
    wherein said perforated plates with associated downpipes comprise a number of open plates between 4 and 25, defined by a degree of perforation p % of between 2% and 6% of the empty cross-section of the column, and a number of closed plates between 1 and 3,
    wherein each closed plate is defined by a degree of perforation between 0.3 and 0.5 times that of the open plates,
    each closed plate is situated between two open plates so that each closed plate is adjacent to two open plates,
    said closed plates are situated in the middle part of the column,
    wherein said downpipes associated with the closed plates have cross-sections between 0.25 and 1 times the cross-sections of the downpipes associated with the open plates, and said downpipe associated with at least one of said closed plates comprises a part crossing the column substantially along the diameter of said column, so that the outlet of said downpipe is located opposite the inlet of said downpipe relative to the cross section of said column.

2. The liquid-liquid extraction column according to claim 1, further comprising a packing layer intended to promote coalescence wherein said packing layer is situated underneath at least one of said closed plates, wherein the thickness of each said packing layer is less than the height of the downpipe associated with the corresponding closed plate.

3. The liquid-liquid extraction column according to claim 1, wherein the number of open plates is between 6 and 20.

4. A method of using the extraction column according to claim 1, for the extraction of sulphur-containing compounds from a hydrocarbon phase by a 10 to 20 wt. % aqueous solution of sodium carbonate, said hydrocarbon phase being a dispersed phase, and wherein said column has a number of theoretical stages between 2 and 4, and within which the partition coefficient of the solute to be extracted is greater than or equal to 50.

5. A method of using the extraction column according to claim 1, in which the ratio of the flow rate of an extract phase (E) to a raffinate phase (R) is between 5 and 50, and wherein said column has a number of theoretical stages between 2 and 4, and within which the partition coefficient of the solute to be extracted is greater than or equal to 50.

6. A method of using the extraction column according to claim 1, in which the ratio of the flow rate of an extract phase (E) to a raffinate phase (R) is between 0.02 and 0.2, and wherein said column has a number of theoretical stages between 2 and 4, and within which the partition coefficient of the solute to be extracted is greater than or equal to 50.

7. A method of using the extraction column according to claim 1, in which the dispersed phase is the light phase, and wherein said column has a number of theoretical stages between 2 and 4, and within which the partition coefficient of the solute to be extracted is greater than or equal to 50.

8. A method of using the extraction column according to claim 1, in which the dispersed phase is the heavy phase, and wherein said column has a number of theoretical stages between 2 and 4, and within which the partition coefficient of the solute to be extracted is greater than or equal to 50.

9. The liquid-liquid extraction column according to claim 1, wherein the number of open plates is between 6 and 25.

10. The liquid-liquid extraction column according to claim 1, wherein the number of closed plates is 1 or 2.

11. The liquid-liquid extraction column according to claim 1, wherein the perforations of an open plate is between 3% and 5% of the empty cross-section of the column.

12. The liquid-liquid extraction column according to claim 3, wherein the number of closed plates is 1 or 2.

13. The liquid-liquid extraction column according to claim 1, wherein there is a first space between a first closed plate and a first open plate positioned directly below said first closed plate and a second space between two successive open plates, and said first space is greater than said second space.

* * * * *